United States Patent
Ruzycki et al.

(10) Patent No.: US 12,193,931 B2
(45) Date of Patent: Jan. 14, 2025

(54) 3D SLA PRINTED CUSTOMIZABLE STAPES PROSTHESIS

(71) Applicant: UNIVERSITY OF FLORIDA RESEARCH FOUNDATION, INCORPORATED, Gainesville, FL (US)

(72) Inventors: Nancy Jean Ruzycki, Bushnell, FL (US); Gavin Carter, Gainesville, FL (US); Brenda A. Burke, Weston, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 319 days.

(21) Appl. No.: 17/639,046

(22) PCT Filed: Aug. 27, 2020

(86) PCT No.: PCT/US2020/048109
§ 371 (c)(1),
(2) Date: Feb. 28, 2022

(87) PCT Pub. No.: WO2021/041610
PCT Pub. Date: Mar. 4, 2021

(65) Prior Publication Data
US 2022/0354636 A1 Nov. 10, 2022

Related U.S. Application Data

(60) Provisional application No. 62/892,248, filed on Aug. 27, 2019.

(51) Int. Cl.
*A61F 2/18* (2006.01)
(52) U.S. Cl.
CPC .......... *A61F 2/18* (2013.01); *A61F 2002/183* (2013.01); *A61F 2240/004* (2013.01)

(58) Field of Classification Search
CPC .................. A61F 2/18; A61F 2002/183; A61F 2240/004; A61F 2240/002
USPC ...................................... 264/210.6
See application file for complete search history.

(56) References Cited

U.S. PATENT DOCUMENTS

| | | |
|---|---|---|
| 4,655,776 A | 4/1987 | Lesinski |
| 2007/0083263 A1 | 4/2007 | Steinhardt et al. |
| 2018/0042718 A1 | 2/2018 | Remenschneider et al. |
| 2018/0116788 A1 | 5/2018 | Kozin et al. |
| 2018/0311035 A1 | 11/2018 | Hirsch et al. |
| 2018/0344894 A1 | 12/2018 | Kay et al. |

FOREIGN PATENT DOCUMENTS

WO 2021041610 A1 3/2021

OTHER PUBLICATIONS

PCT/US2020/048109, PCT Search Report & Written Opinion mailed Dec. 22, 2020, 9 pages.
Pudlik, Malgorzata et al., "Chamber stapes prosthesis with an improved fastening of the membrane", ITM web Conferences, 2017, vol. 15, No. 05005.

*Primary Examiner* — Hannah J Pak
(74) *Attorney, Agent, or Firm* — Timothy H. Van Dyke; Wolter Van Dyke Davis, PLLC

(57) ABSTRACT

Methods for producing a custom-made stapes prosthesis for a patient and stapes prostheses so produced. The methods may include obtaining a three-dimensional image of a natural stapes bone of the patient; and forming a stapes prosthesis that closely approximates a three-dimensional shape of the natural stapes bone via an additive manufacturing technique based on the three-dimensional image. The stapes prosthesis comprises a suitable material that is not osteogenic and is not cytotoxic. The stapes prosthesis may include a plurality of pores having an average size of from about 5 to about 100 micrometers and may exhibit a frequency of sound transmission in a range of from about 2 to about 30 kilohertz.

9 Claims, 14 Drawing Sheets

3D SLA PRINTED CUSTOMIZABLE STAPES PROSTHESIS

CROSS-REFERENCE TO RELATED APPLICATION

This application claims the benefit of U.S. Provisional Patent Application No. 62/892,248, filed Aug. 27, 2019, titled 3D SLA PRINTED CUSTOMIZABLE STAPES PROSTHESIS, which is incorporated by reference herein in its entirety.

BACKGROUND

The stapes or stirrup is a bone in the middle ear of humans and other mammals which is involved in the conduction of sound vibrations to the inner ear. The stirrup-shaped small bone is on and transmits these to the oval window, medially. The stapes is the smallest and lightest named bone in the human body and is so-called because of its resemblance to a stirrup.

Otosclerosis is a congenital or spontaneous-onset disease characterized by abnormal bone remodeling in the inner ear. Often this causes the stapes to adhere to the oval window, which impedes its ability to conduct sound, and is a cause of conductive hearing loss. Clinical otosclerosis is found in about 1% of people, although it is more common in forms that do not cause noticeable hearing loss. Otosclerosis is more likely in young age groups, and females. Two common treatments are stapedectomy, the surgical removal of the stapes and replacement with an artificial prosthesis, and stapedotomy, the creation of a small hole in the base of the stapes followed by the insertion of an artificial prosthesis into that hole. Surgery may be complicated by a persistent stapedial artery, fibrosis-related damage to the base of the bone, or obliterative otosclerosis, resulting in obliteration of the base.

Current prosthetic models are standardized and are not even shaped like the human stapes, let alone the stapes of a particular patient. A need, therefore, exists for an improved stapes prosthesis.

The discussion of shortcomings and needs existing in the field prior to the present invention is in no way an admission that such shortcomings and needs were recognized by those skilled in the art prior to the present disclosure.

BRIEF SUMMARY

Various embodiments relate to a method for producing a custom-made stapes prosthesis for a patient. The method may comprise: obtaining a three-dimensional image of a natural stapes bone of the patient; and forming a stapes prosthesis that closely approximates a three-dimensional shape of the natural stapes bone via an additive manufacturing technique based on the three-dimensional image. The stapes prosthesis may comprise a suitable material that is not osteogenic and is not cytotoxic. The stapes prosthesis may include a plurality of pores having an average size of from about 5 to about 100 micrometers and may exhibit a frequency of sound transmission in a range of from about 2 to about 30 kilohertz. According to certain embodiments, the additive manufacturing technique may be 3D printing, including but not limited to 3D SLA printing.

The suitable material may have a variety of special properties. For example, according to various embodiments, the suitable material may have a density of from about 700 to about 2000 kg/m$^3$; a rigidity modulus of from about 1.75 to about 8.00 GPa; a Young's modulus of from about $1\times10^{10}$ to about $2\times10^{10}$ N m$^{-2}$; a shear modulus that changes from about 3.6 to about 220 kPa when an applied shear stress increases from about 2 to about 140 kPa; and/or a specific mass of from about $1\times10^3$ to about $3\times10^3$ kg/m$^3$. Additionally or alternatively, ultrasound waves may be able to propagate through the suitable material at a velocity of from about 1,000 m/s to about 2,300 m/s. According to various embodiments, the suitable material may be a polymeric material selected and customized to ensure that the specific property requirements are met. In some cases, the polymeric material may be a polyurethane, such as a foam polyurethane, or a high-density polyethylene, such as a high-density polyethylene sponge material.

Various embodiments relate to a stapes prosthesis comprising a head; a neck; at least one connecting crus; a base, the head being structurally associated with the neck, the neck being structurally associated with the base via the at least one connecting crus, wherein each of the head, the neck, the at least one connecting crus, and the base comprise a suitable material. The suitable material may be as described above or herein. The stapes prosthesis may comprise a plurality of pores having an average size of from about 5 to about 100 micrometers and may exhibit a frequency of sound transmission in a range of from about 2 to about 30 kilohertz.

These and other features, aspects, and advantages of various embodiments will become better understood with reference to the following description, figures, and claims.

BRIEF DESCRIPTION OF THE FIGURES

Many aspects of this disclosure can be better understood with reference to the following figures.

Figure 1:
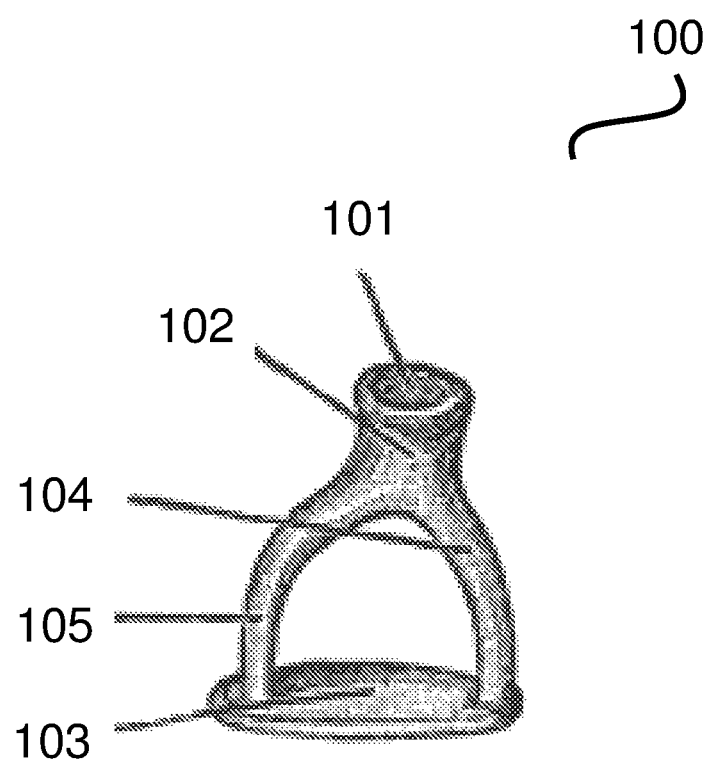
FIG. 1 is an example according to various embodiments, illustrating a 3D printed stapes prosthesis.

It should be understood that the various embodiments are not limited to the examples illustrated in the figures.

DETAILED DESCRIPTION

Introduction and Definitions

Various embodiments may be understood more readily by reference to the following detailed description. Unless defined otherwise, all technical and scientific terms used herein have the same meaning as commonly understood by one of ordinary skill in the art to which this disclosure belongs.

As used herein, "SLA" refers to stereolithography (also known as optical fabrication, photo-solidification, or resin printing), which is a form of 3D printing technology used for creating models, prototypes, patterns, and production parts in a layer by layer fashion using photochemical processes by which light causes chemical monomers and oligomers to cross-link together to form polymers.

As used herein, the term "standard temperature and pressure" generally refers to 25° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C.

The term "mol percent" or "mole percent" generally refers to the percentage that the moles of a particular component are of the total moles that are in a mixture. The sum of the mole fractions for each component in a solution is equal to 1.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure.

General Discussion

Various embodiments described herein relate to a stapes prosthesis that may be shaped like a human stapes. The stapes prostheses according to various embodiments may be manufactured by any suitable means, such as via an additive manufacturing process. The additive manufacturing process may be a computer-aided 3D printing process, based on a three-dimensional model of the desired stapes prosthesis.

FIG. 1 is an example according to various embodiments, illustrating a stapes prosthesis 100. The prosthesis 100 may be shaped like a human stapes and may include a head 101, a neck 102, and a base 103. The head 101 may be directly structurally associated with the neck 102. The neck 102 may be structurally associated with the base 103 via one or more crus, such as, an anterior crus 104 and a posterior crus 105.

Figure 2:
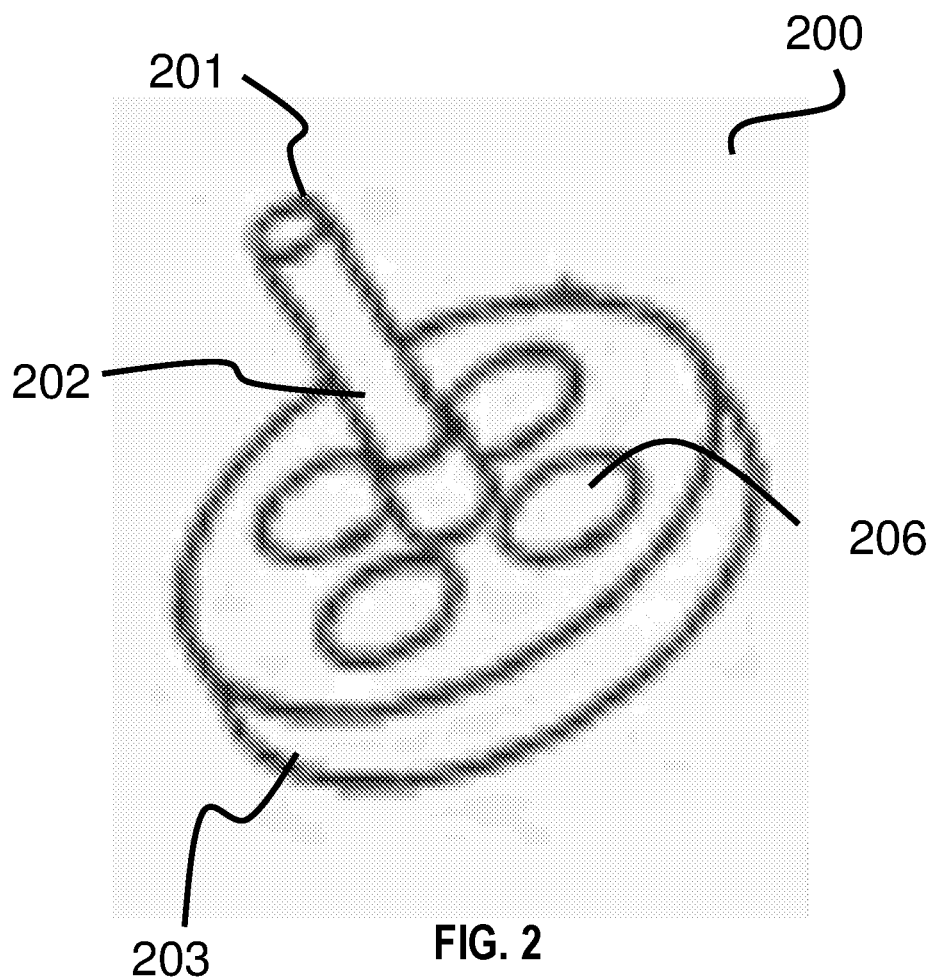
FIG. 2 is an example according to various embodiments, illustrating a drawing for a prototype of a stapes prosthesis.

FIG. 2 is an example according to various embodiments, illustrating a stapes prosthesis 200. The prosthesis 200 may include a head 201, a neck 202, and a base 203. The head 201 may be directly structurally associated with the neck 202. The neck 202 may be directly structurally associated with the base 203. The base 203 may include one or more through-holes 206, extending therethrough.

The three-dimensional model may be designed using readily available computer-aided drafting software and the particular design of the prosthesis may be based on one or more medical images of a human stapes. The medical images may be for a specific patient, for whom the prosthesis is being custom-made. Alternatively, the medical images may be for a plurality of patients and the resulting design may be a one-size-fits-all averaged design to accommodate a large percentage of the population. The medical imaging may provide the template model which can be translated to CAD software and printed providing a custom stapes prosthesis, made of an additive manufacturing material such as a polymer more closely related to tissue than the current metal models.

Various embodiments relate to a stapes prosthesis that includes a head, a neck, an anterior crus, a posterior crus, and a base. The head may be structurally associated with the neck, and the neck may be structurally associated with the base via the anterior crus and the posterior crus. Each of the head, the neck, the anterior crus, the posterior crus, and base may include a suitable material. A variety of suitable materials may be employed. According to various embodiments, the suitable material is not osteogenic, is not cytotoxic, and is suitable for use in additive manufacturing processes.

A suitable material may be composed of materials which will not be cytotoxic after printing and post-production curing. There are a range of polymers currently available for use in dental applications which could prove sufficient for use in 3D printing of stapes prostheses.

The stapedial annular ligament (SAL) lies in the gap between the stapes footplate and the margin of the oval window which has mechanical properties for Young's modulus which varies with stress level but is assumed to be in the range of about $1.41 \times 10^{10}$ N m$^{-2}$. The human SAL is a typical viscoelastic material with hysteresis, nonlinear stress-strain relationship and stress relaxation function. The shear modulus changes from about 3.6 to about 220 kPa when the shear stress increases from about 2 to about 140 kPa. The specific mass is estimated to be about $2.2 \times 10^3$ kg/m$^3$.

Sound induced stapes velocity changes with the frequency of sound. Literature reported values indicate that mean Vs is stiffness-dominated at frequencies below 1 kHz, increased up to ~4 kHz, and then decreased at higher frequencies. The phase of the mean velocity was +0.2 periods at 0.3 kHz, and gradually became a phase lag at higher frequencies. The mean Vs is reported to be about 40 micrometers/sec/Pa at 1000 Hz frequency. The outer and middle ears amplify sound on its passage from the exterior to the inner ear by about 15-30 dB.

Various embodiments relate to a stapes prosthesis that may include a head; a neck; an anterior crus; a posterior crus; and a base. The head may be structurally associated with the neck. The neck may be structurally associated with the base via the anterior crus and the posterior crus. Each of the head, the neck, the anterior crus, the posterior crus, and the base may include a suitable material. The suitable material may mimic the material properties of a naturally occurring structure as described above. According to various embodiments, the suitable material is not osteogenic. According to various embodiments, the suitable material is not cytotoxic. According to various embodiments, the suitable material is suitable for use in additive manufacturing processes. Photoinitated polymers commonly used in 3D printing have tensile strengths of around 40 MPa and a glass transition of around 110 C, Young's modulus of around 15-1800 MPa, Shore Hardness of 30-95.

Suitable materials for use in the methods according to various embodiments and from which the stapes prostheses according to various embodiments may be made have a variety of specialized properties. A suitable material may exhibit any or all of the specialized properties described herein in association with any embodiment.

The suitable material may be non-osteogenic, meaning that it does not readily result in the formation of bone. The suitable material may be non-cytotoxic, meaning that it is non-toxic to living cells. According to various embodiments, the suitable material is not osteogenic and does not promote cell or bone growth. The middle cavity of the ear is an air-filled vessel and the material should not experience water gain or mass owing to the environment. Suitable materials may include, methyl(methacrylate)polymers, polyurethane foams, and polyethylene foams.

The suitable material may comprise a plurality of pores having an average size of from about 5 to about 100 micrometers. Similarly, since the stapes prosthesis according to various embodiments comprises the suitable material, the stapes prosthesis may comprise a plurality of pores having an average size of from about 5 to about 100 micrometers. According to various embodiments, the suitable material and/or the stapes prosthesis may comprise a plurality of pores having an average size of from about 5 to about 100 micrometers Each range described herein is intended to include all numerical values encompassed by the range. Furthermore, additional ranges may be formed from any lower limits and/or upper limits described herein. For example, according to various embodiments, the suitable material and/or the stapes prosthesis may comprise a plurality of pores having an average size within a range having a lower limit and/or an upper limit. The range may include or exclude the lower limit and/or the upper limit. By way of example and not limitation, a lower limit and/or an upper limit may be selected from 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145 and 150 micrometers. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, according to various embodiments, the suitable material and/or the stapes prosthesis may comprise a plurality of pores having an average size of: about 1 to about 150 micrometers, less than about 1 micrometers, greater than about 1 micrometers, less than about 150 micrometers, or greater than about 150 micrometers, etc. All such ranges are contemplated and are intended to be explicitly disclosed and recited. Each value recited is intended to be modified by the term "about." As used herein the term "size" generally refers to the average cross-sectional diameter of a given pore. The term "average size" refers to the average of all sizes of pores within a set of pores.

According to various embodiments, the stapes prosthesis may exhibit a frequency of sound transmission in a range of from about 2 to about 30 kilohertz. Each range described herein is intended to include all numerical values encompassed by the range. Furthermore, additional ranges may be formed from any lower limits and/or upper limits described herein. For example, the stapes prosthesis may exhibit a frequency of sound transmission within a range having a lower limit and/or an upper limit. The range may include or exclude the lower limit and/or the upper limit. By way of example and not limitation, a lower limit and/or an upper limit may be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 kilohertz. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, the stapes prosthesis may exhibit a frequency of sound transmission of: about 1 to about 40 kilohertz, less than about 1 kilohertz, greater than about 1 kilohertz, less than about 40 kilohertz, or greater than about 40 kilohertz, etc. All such ranges are contemplated and are intended to be explicitly disclosed and recited. Each value recited is intended to be modified by the term "about."

According to various embodiments, the suitable material hay have a density of from about 700 to about 2000 $kg/m^3$. Each range described herein is intended to include all numerical values encompassed by the range. Furthermore, additional ranges may be formed from any lower limits and/or upper limits described herein. For example, the suitable material have a density within a range having a lower limit and/or an upper limit. The range may include or exclude the lower limit and/or the upper limit. By way of example and not limitation, a lower limit and/or an upper limit may be selected from 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450 and 2500 $kg/m^3$. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, the suitable material hay have a density of: about 500 to about 2500 $kg/m^3$, less than about 500 $kg/m^3$, greater than about 500 $kg/m^3$, less than about 2500 $kg/m^3$, or greater than about 2500 $kg/m^3$, etc. All such ranges are contemplated and are intended to be explicitly disclosed and recited. Each value recited is intended to be modified by the term "about."

According to various embodiments, the suitable material may have a rigidity modulus of from about 1.75 to about 8.00 GPa. Each range described herein is intended to include all numerical values encompassed by the range. Furthermore, additional ranges may be formed from any lower limits and/or upper limits described herein. For example, the suitable material may have a rigidity modulus within a range having a lower limit and/or an upper limit. The range may include or exclude the lower limit and/or the upper limit. By way of example and not limitation, a lower limit and/or an upper limit may be selected from 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75 and 10 GPa. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, the suitable material may have a rigidity modulus of: about 1 to about 10 GPa, less than about 1 GPa, greater than about 1 GPa, less than about 10 GPa, or greater than about 10 GPa, etc. All such ranges are contemplated and are intended to be explicitly disclosed and recited. Each value recited is intended to be modified by the term "about."

According to various embodiments, ultrasound waves may be able to propagate through the suitable material at a velocity of from about 1,000 m/s to about 2,300 m/s. Each range described herein is intended to include all numerical values encompassed by the range. Furthermore, additional ranges may be formed from any lower limits and/or upper limits described herein. For example, ultrasound waves may be able to propagate through the suitable material at a velocity within a range having a lower limit and/or an upper limit. The range may include or exclude the lower limit and/or the upper limit. By way of example and not limitation, a lower limit and/or an upper limit may be selected from 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450 and 2500 m/s. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, ultrasound waves may be able to propagate through the suitable material at a velocity of: about 750 to about 2500 m/s, less than about 750 m/s, greater than about 750 m/s, less than about 2500 m/s, or greater than about 2500 m/s, etc. All such ranges are contemplated and are intended to be explicitly disclosed and recited. Each value recited is intended to be modified by the term "about."

According to various embodiments, the suitable material may have a Young's modulus of from about $1 \times 10^{10}$ to about $2 \times 10^{10}$ N·m$^{-2}$. Each range described herein is intended to include all numerical values encompassed by the range.

According to various embodiments, the suitable material may have a specific mass of from about $1 \times 10^3$ to about $3 \times 10^3$ kg/m$^3$. Each range described herein is intended to include all numerical values encompassed by the range.

According to various embodiments, the suitable material may exhibit a shear modulus that changes from about 3.6 to about 220 kPa when an applied shear stress increases from about 2 to about 140 kPa. Each range described herein is intended to include all numerical values encompassed by the range.

According to various embodiments, the suitable material may be a polymeric material selected and customized to ensure that the specific property requirements are met. In some cases, the polymeric material may be a polyurethane, such as a foam polyurethane, or a high-density polyethylene, such as a high-density polyethylene sponge material. Plastipore® and Poly-Cel® may be used as suitable materials according to various embodiments. These materials have pore diameters of 20 to 40 micrometer, encouraging tissue ingrowth aiming to stabilize the anchorage of the implant.

The suitable material should not be a blend of polyether urethane, polypropylene oxide and polyether polyester copolymer as these materials were found to be incompatible during rat model studies. The material should not be hydroxyapatite ceramic material owing to studies showing it was incompatible. It should not be an Ionomer cement material, as these also have been shown to be incompatible in rat model studies.

The suitable material may be any suitable polymer, including various thermoplastic, thermosetting, and photoinitiated polymers. Most additive manufacturing materials, including many polymers, are not osteogenic in that they do not have the same properties as natural bone, and may be derived from monomers which are cytotoxic. The polymer may be selected properties of a naturally occurring to provide similar mechanical and/or acoustical human stapes. A suitable polymer may have a high degree of crosslinking. A suitable polymer may not have leaching of monomers after curing. Selection of a suitable additive manufacturing material must include consideration of many issues, including but not necessarily limited to water uptake, abrasion resistance, leaching of monomers, toxicity, and a potentially high cost for biocompatible polymer formulations. Various other considerations may arise based on the particular additive manufacturing process employed, such as potential issues with a 3D printer printing the selected material, which may include but are not necessarily limited to window interactions, cure speed, viscosity, and shear interactions.

Various embodiments relate to a method for producing a custom-made stapes prosthesis for a patient. The method may comprise obtaining a three-dimensional image of a natural stapes bone of the patient. The three-dimensional image may be obtained by any suitable method, such as any medical imaging technique. The three-dimensional image may be used as a model to guide an additive manufacturing process. The additive manufacturing process may be, but is not limited to 3D printing or 3D SLA printing.

For example, according to various embodiments, the method may further include using a suitable material to form a stapes prosthesis that closely approximates a three-dimensional shape of the natural stapes bone via an additive manufacturing technique based on the three-dimensional image. The additive manufacturing technique may be 3D printing in which the suitable material is added layer-by-layer. The suitable material may be any suitable material described herein according to any of the various embodiments. According to other embodiments, the method may further include forming a stapes prosthesis that closely approximates a three-dimensional shape of the natural stapes bone via an additive manufacturing technique based on the three-dimensional image, wherein the stapes prosthesis comprises a suitable material that is not osteogenic and is not cytotoxic. The additive manufacturing technique may be 3D SLA printing, in which in the stapes prosthesis is formed in a layer by layer fashion using photochemical processes by which light causes chemical monomers and oligomers to cross-link together to form polymers. These resulting polymers may be the "suitable material" referenced according the various embodiments. The suitable materials so produced may have any or all of the properties as described according to any of the various embodiments.

EXAMPLES

Introduction

The following examples are put forth to provide those of ordinary skill in the art with a complete disclosure and description of how to perform the methods, how to make, and how to use the compositions and compounds disclosed and claimed herein. Efforts have been made to ensure accuracy with respect to numbers (e.g., amounts, temperature, etc.), but some errors and deviations should be accounted for. The purpose of the following examples is not to limit the scope of the various embodiments, but merely to provide examples illustrating specific embodiments.

Example 1

A purpose of this example is to demonstrate procedures employed and results obtained for a particular stapes prosthesis according to various embodiments. An emphasis is placed on evaluating the mechanical characteristics and results for a particular photopolymer. The photopolymer used was PR-48 Standard Clear from Colorado Photopolymer Solutions, LLC. This polymer is a photosensitive material commonly used for 3D printing. The precise formulation is not available as it is proprietary.

The stapes prosthesis manufactured had the structure as shown in FIG. 2, sized for middle ear dimensions. The structure was designed in a 3D CAD software package sold under the trademark, SOLIDWORKS®. The prosthesis was printed using an AUTODESK® Ember SLA printer. The exposure time and layer thickness varied. A post-printing cure and crosslinking was conducted using a THERMO FISHER® FB-UXL-1000. A visual analysis was conducted using a ZEISS® Stereoscope and ImageJ. Fourier-transform Infrared Spectroscopy (FTIR) was performed using a spectroscope from THERMO FISCHER® to measure an extent of crosslinking.

The following is a summary of various printing parameters, including time and layer parameters.

Time Parameters
  (constant parameters–Layer 0.025 mm, $Z_{lift}$=0.75 mm, AR=60°, ASV=12 RPM, AZV=1.5 mm/s)
  4, 6, 8, 10, 12, 14, 16 seconds
  Post-cure=5 mins (120,000 microjoules)

Layer Parameters
  (constant parameters–time 8 secs, same as above)
  0.005, 0.01, 0.015, 0.02, 0.025, 0.03, 0.035, 0.04, 0.045, 0.05 millimeters The parameters above are the ones used in the experimentation. Within the SLA printer, there are more than 30 settings which may be adjusted to optimize printing of the prosthesis. The specific parameters were obtained through user sourced concerns along with adjustments made to the print in order to solve the problem. It was found that layer thickness and exposure time were the two main sources of error in prints that's user of the Ember SLA 3D printer reported. The various other parameters were studied but these two showed the most significant difference in the print, especially exposure time since it correlates to crosslinking. The layer parameter affects the final resolution of the piece itself, hence the smaller the layers the more difficulties can arise within the print in relation to crosslinking or layer adhesion/formation. The values for the time parameter and layer parameter are in seconds and millimeters, respectively. The standard time for the time parameter and layer parameters was 8 seconds and 0.025 millimeters, respectively, and the other test values were obtained by doubling and halving the standard value to obtain the maximum and minimum test value, respectively. For time parameters it changes by 2 seconds and the Layer Parameters changes by 0.005 millimeters. Layer thickness is an important parameter as 3D photoinitiated resins include light blocking chemicals to reduce layer curing for the material in the layers above the current printed layer. PR48 is designed to work best at a layer thickness of 25 microns, and if the layer thickness is adjusted, the light exposure time must be adjusted as well.

In general the 3D printing cycle for SLA printers involves printer rotation to the PDMS layer at a set approach slide velocity at which point the build head lowers and comes into contact with PDMS at the approach Z-axis velocity, irradiates the sample design on the build head for a set exposure time, then rotates back through an angle of rotation to the height based on the Z-axis overlift setting with the specified separation slide velocity. Pauses can be inserted into the cycle for wait time after light exposure, separation or approach. The main settings changed in the optimization of the print include; exposure time (seconds), Separation Slide Velocity (SSV (RPM)), Approach Slide Velocity(ASV (RPM)), Z-axis Overlift ($Z_{lift}$ (microns)), Separation Z-axis Velocity (microns/s), Approach Z-axis Velocity (AZV (microns/s), Angle of Rotation(AR (millidegrees), Wait times (miliseconds). While all of these parameters were adjusted to optimize the printing of the prosthesis, only the ones found to effect the print quality are reported here.

Figure 3:
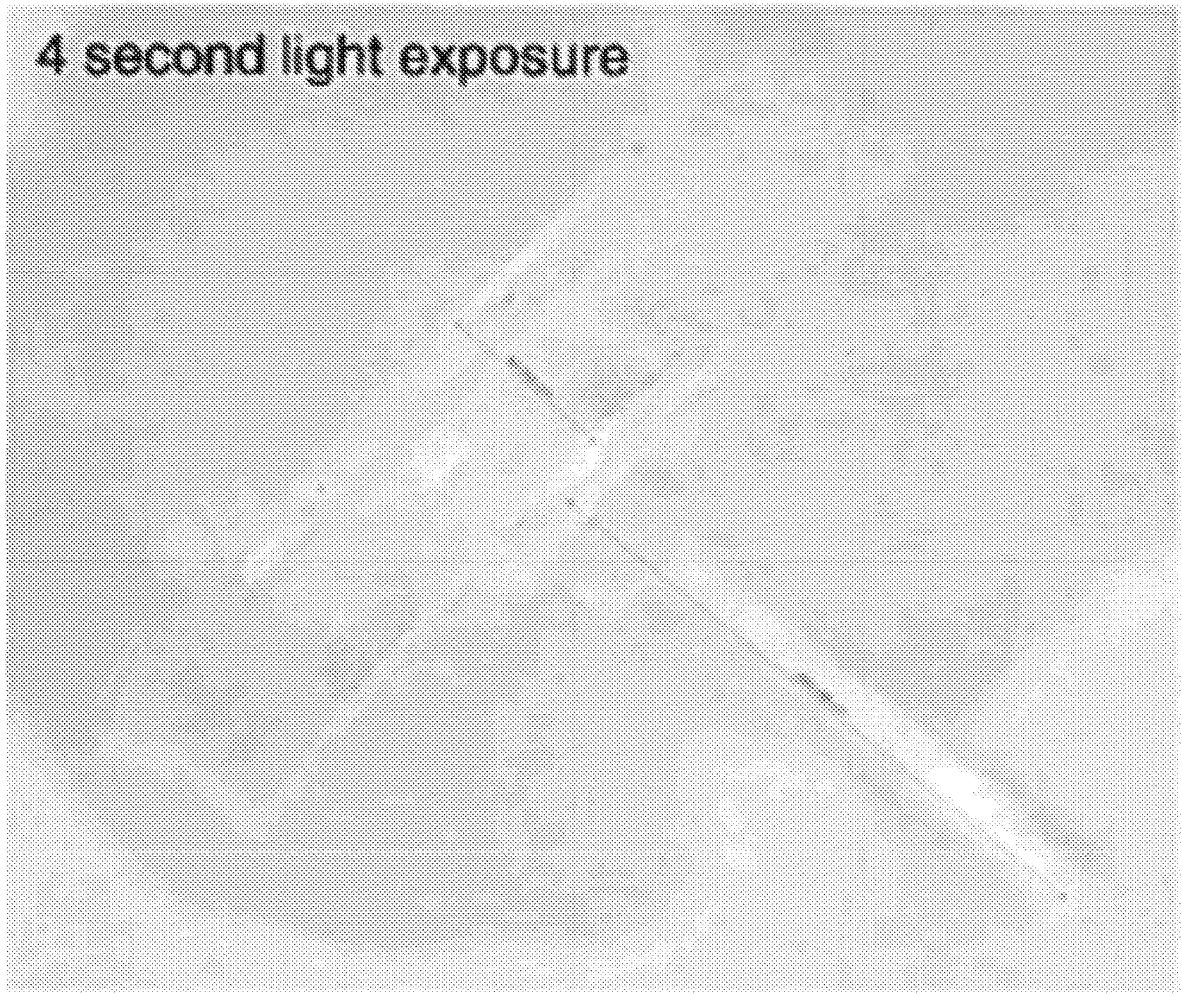
FIG. 3 is an example according to various embodiments illustrating a photograph of a printed stapes prosthesis printed with a 4-second light exposure time and a visible defect noted as layer shifting.
Figure 4:
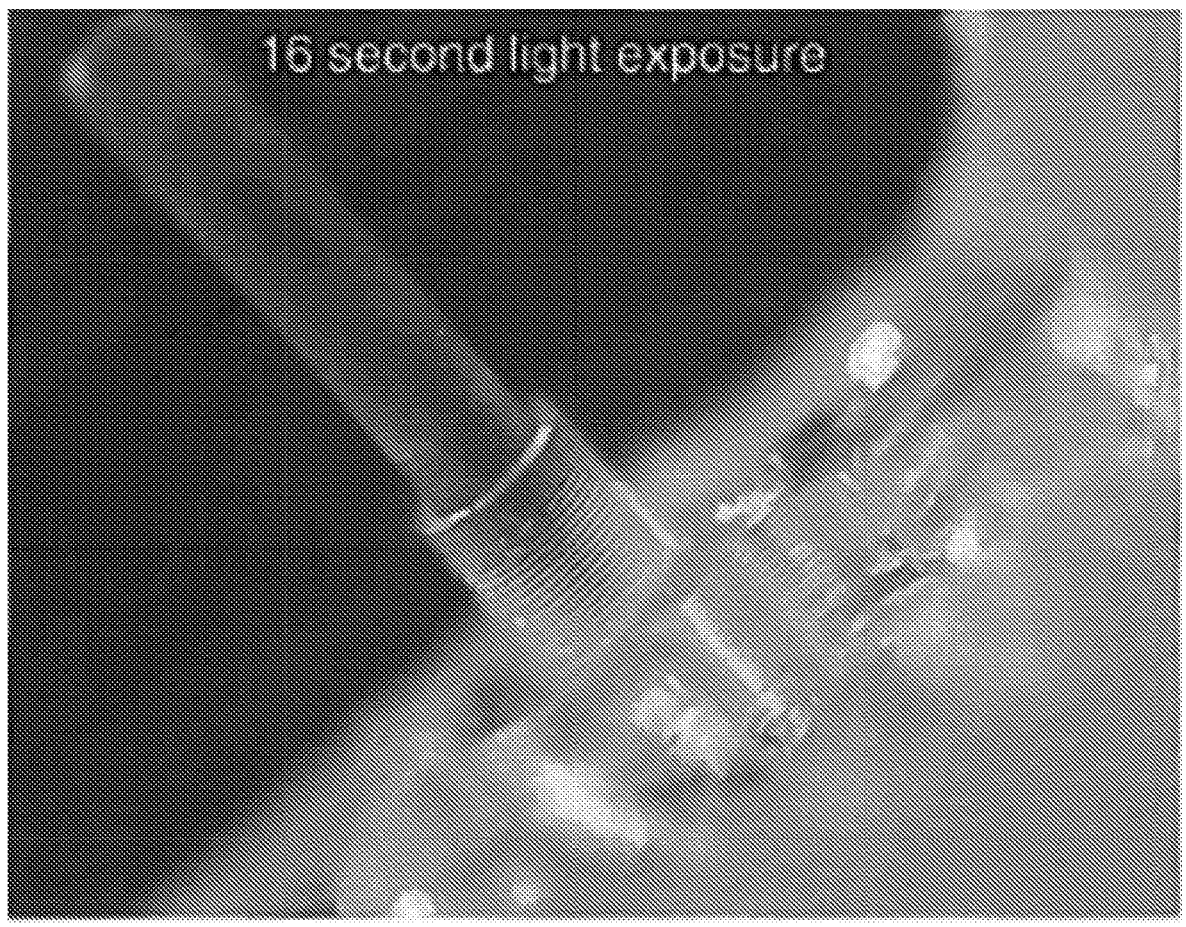
FIG. 4 is an example according to various embodiments illustrating a photograph of a printed stapes prosthesis made by a 16-second light exposure print with nearly perfect symmetry with the noticeable issue of fracturing on the bottom right corner of the image.
Figure 11:
FIG. 11 is an example according to various embodiments of a Zeiss microscope imaged sample after 8 seconds of exposure time along with a scale bar.
Figure 12A:
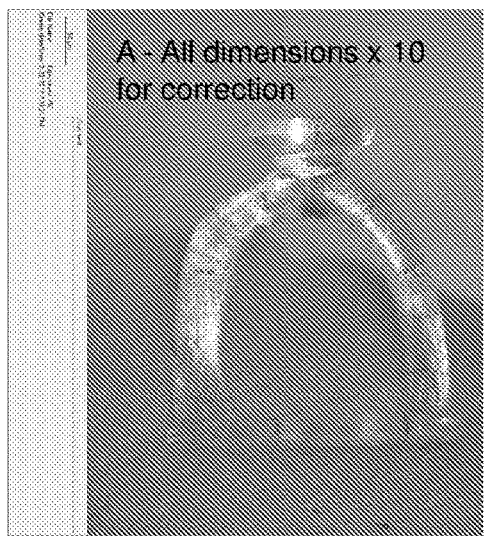
FIG. 12A is an example according to various embodiments of a Zeiss microscope imaged sample after 8 seconds of exposure time.
Figure 12B:
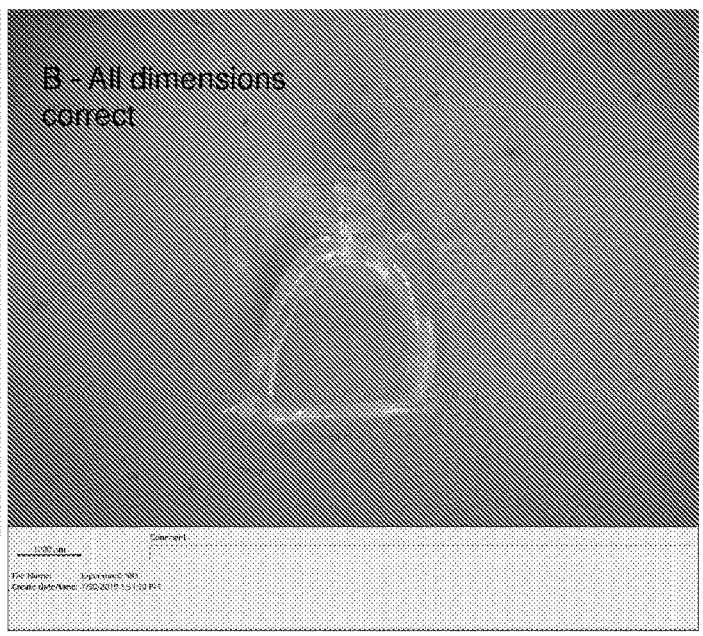
FIG. 12B is an example according to various embodiments of the same image in FIG. 11 but flipped to the opposite side along with scale bar.
Figure 13:
FIG. 13 is an example according to various embodiments of the same image in FIG. 12, but with certain dimensions annotated to compare for dimensional accuracy.
Figure 14:
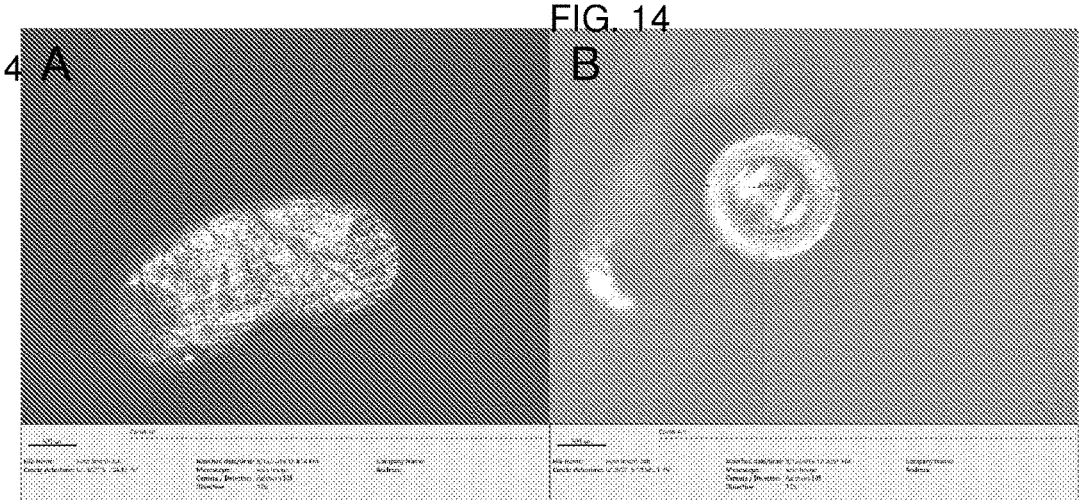
FIG. 14A is an example according to various embodiments of a Zeiss microscope image showing a bottom view of a stapes prosthesis.
FIG. 14B is an example according to various embodiments of a Zeiss microscope image showing a top view of a stapes prosthesis.
FIG. 14C is an example according to various embodiments of a Zeiss microscope image showing a side view of a stapes prosthesis.
Figure 14:
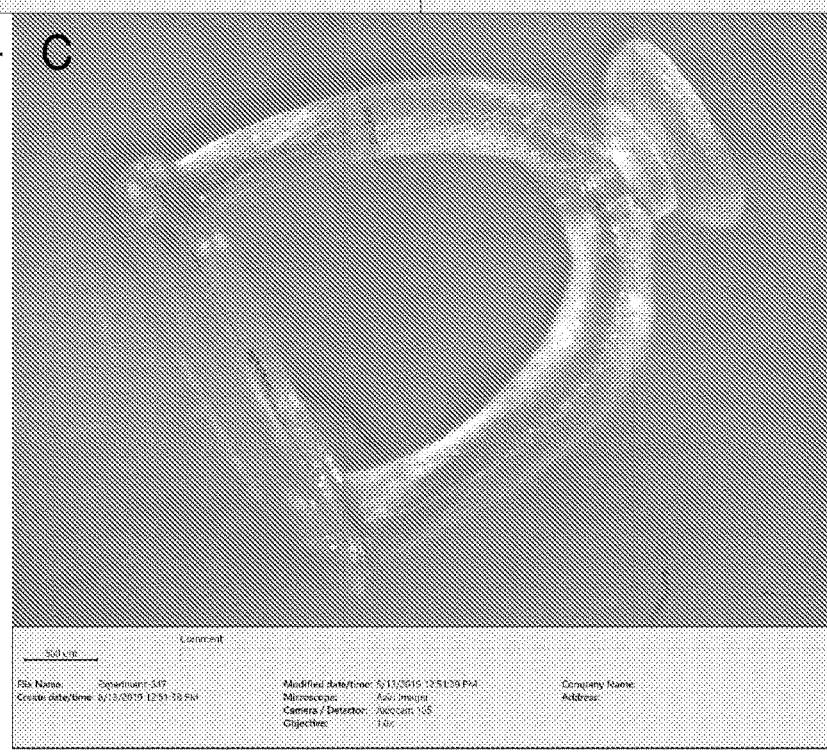

FIG. 3 is an example according to various embodiments illustrating a photograph of a printed stapes prosthesis printed with a 4-second light exposure time and a visible defect noted as layer shifting. FIG. 4 is an example according to various embodiments illustrating a photograph of a printed stapes prosthesis made by a 16-second light exposure print with nearly perfect symmetry with the noticeable issue of fracturing on the bottom right corner of the image. This fracturing is due to the removal process which can be optimized with further or separate testing. FIG. 11 is an example according to various embodiments of a Zeiss microscope imaged sample after 8 seconds of exposure time along with a scale bar. FIG. 12 is an example according to various embodiments of the same image in FIG. 11 but flipped to the opposite side along with scale bar. FIG. 13 is an example according to various embodiments of the same image in FIG. 12, but with certain dimensions annotated to compare for dimensional accuracy.

These images account for the first embodiment of this prosthetic design. An original design was significant for the attempt to print a design which represents currently marketed models including the holes. It improved understanding of the effects of changing exposure time and layer parameters, as well as tray slide velocity. It also allowed for testing the printing process on a simpler design with a more uniform shape rather then start on something with a nonuniform shape. The specific pictures are also visual examples of some the issues we were facing in our original testing and how these issues were resolved in order to produce a more naturally shaped prosthesis.

Dimensional accuracy was obtained at all exposure times for the 3D-printed stapes prosthesis relative to the CAD drawing. The Fourier-transform Infrared Spectroscopy (FTIR) data illustrated in FIGS. 5 and 6 shows that all prints indicate increased crosslinking owing to post-processing UV treatment.

Figure 5:
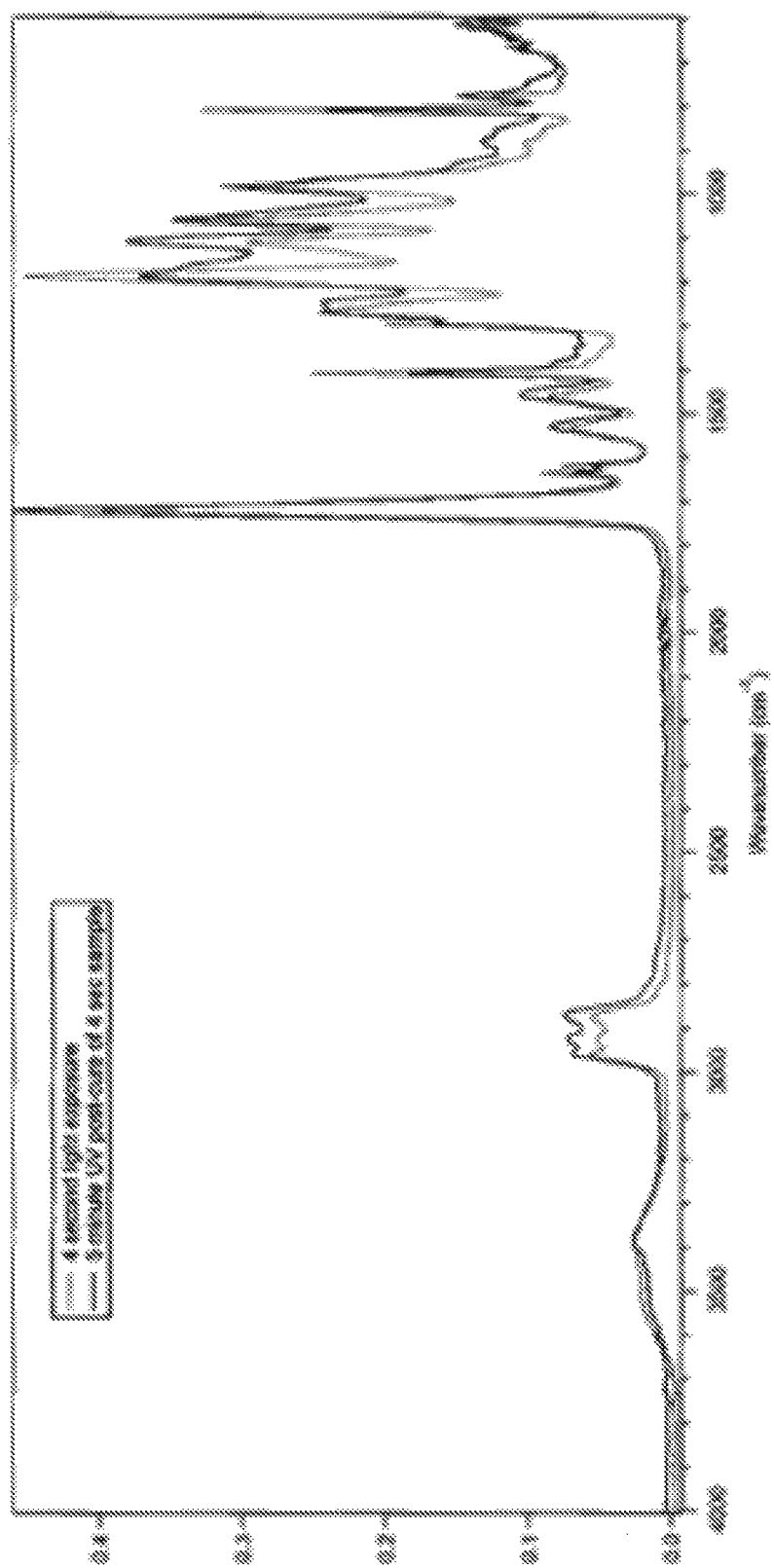
FIG. 5 is an example according to various embodiments illustrating Fourier-transform Infrared Spectroscopy (FTIR) results obtained after light exposure treatment for a 4 second prosthetic print with a 5 min post cure in an Ultraviolet oven.
Figure 6:
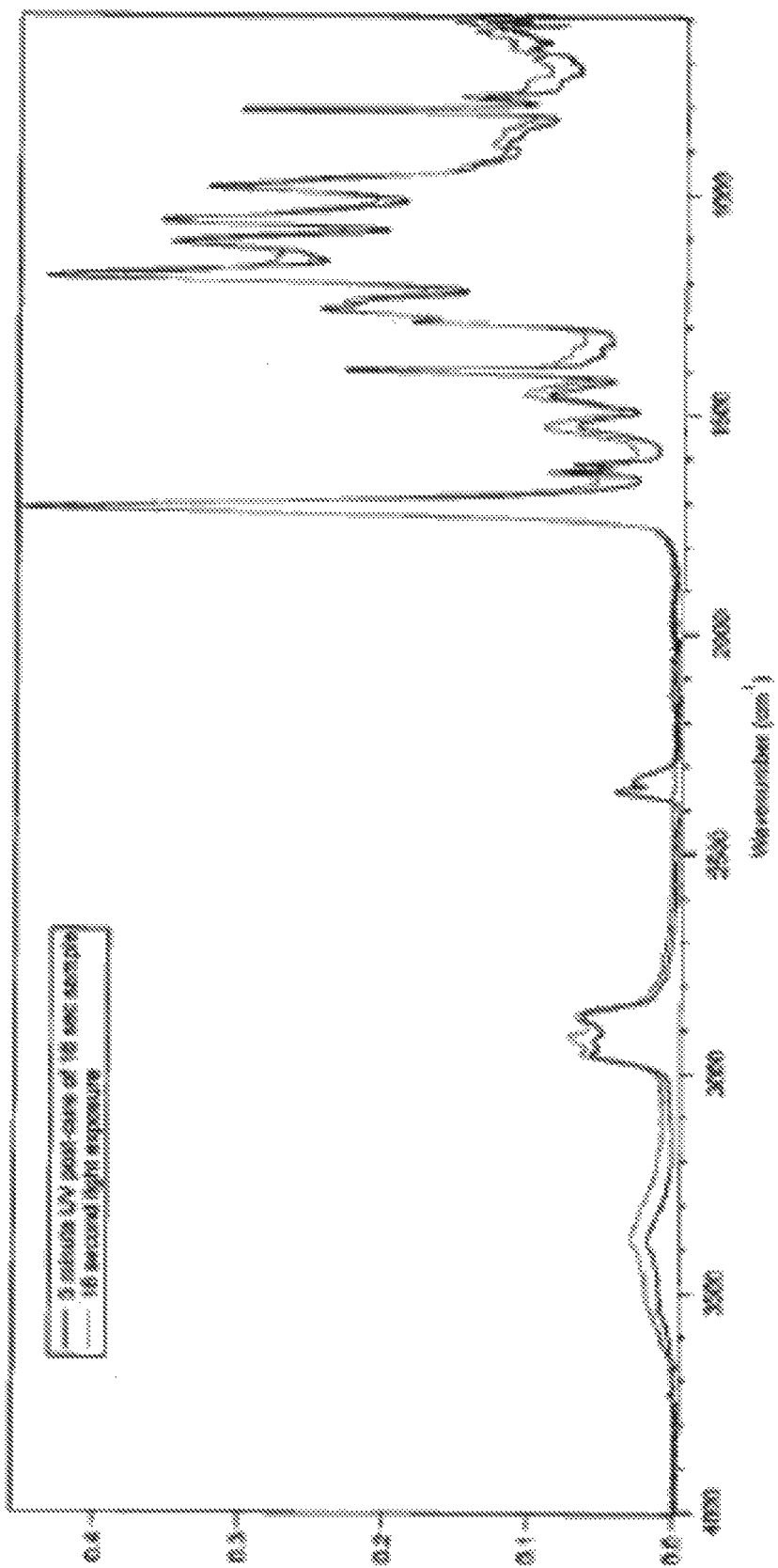
FIG. 6 is an example according to various embodiments illustrating Fourier-transform Infrared Spectroscopy (FTIR) experiment results obtained after 16 seconds exposure and 5 minutes of post-cure UV treatment.

FIG. 5 is an example according to various embodiments illustrating Fourier-transform Infrared Spectroscopy (FTIR) results obtained after light exposure treatment for a 4 second prosthetic print with a 5 min post cure in an Ultraviolet oven. The data was plotting atop one another to analyze the differences in treatment times. The results are further summarized in Table 1. Table 1 gives an overview of the FTIR absorption frequencies for the molecular vibrations which provide key information to the crosslinking of the polymer for as printed and post cured. Understanding of the amount of crosslinking is achieved by comparing the characteristic shapes and patterns within sample spectrum to published group frequency data along with other chemical and physical data. Both the presence, attenuation and absence of bands provides information as to the degree of material crosslinking. The groups presented in Table 1 are related to signatures of linkages known to be in PR48. Attenuation of some of these linkages are related to degree of crosslinking in the material.

TABLE 1

| Molecule | Wave Number ($cm^{-1}$) |
|---|---|
| —OH Hydroxyl groups | ~3400 |
| —C=C aromatic groups | ~1630 |
| —C—O—C Ether groups | ~1070 |
| —C—$CH_2$ groups | Twisting about 812 |
|  | Deformation about 1400 |
| —N—H stretch | ~3100-3500 |
| —C—H $sp^3$ stretch | ~2800-2900 |
| —C=O Ester stretch | ~1750 |

FIG. 6 is an example according to various embodiments illustrating Fourier-transform Infrared Spectroscopy (FTIR) experiment results obtained after 16 seconds exposure and 5 minutes of post-cure UV treatment. The data is plotted atop one another in order to analyze the differences. This 16-second print indicated development of carbonyl groups during post-processing UV cure. Without wishing to be bound by theory, this may have been due to degradation of the resin.

Figure 7:
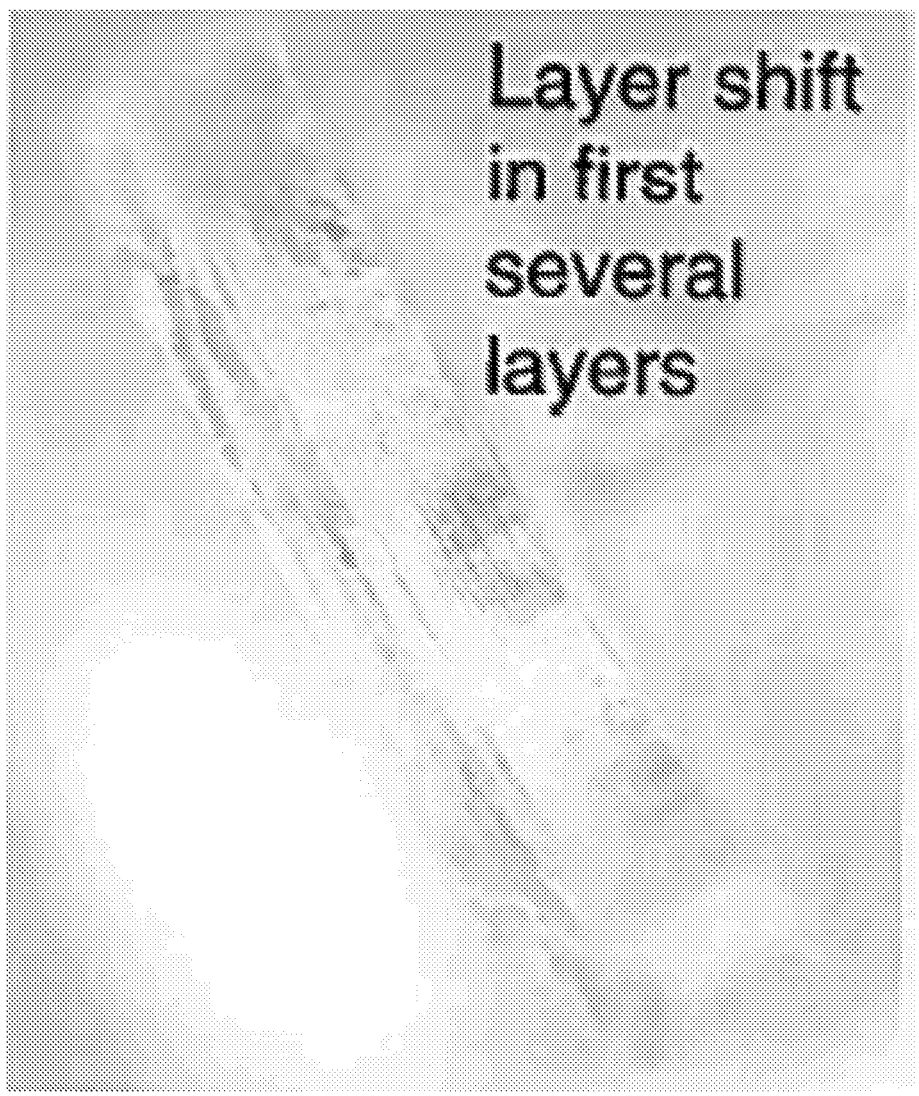
FIG. 7 is an example according to various embodiments illustrating a photograph of a side view of the prosthesis showing a layer shift in the first several layers.
Figure 8:
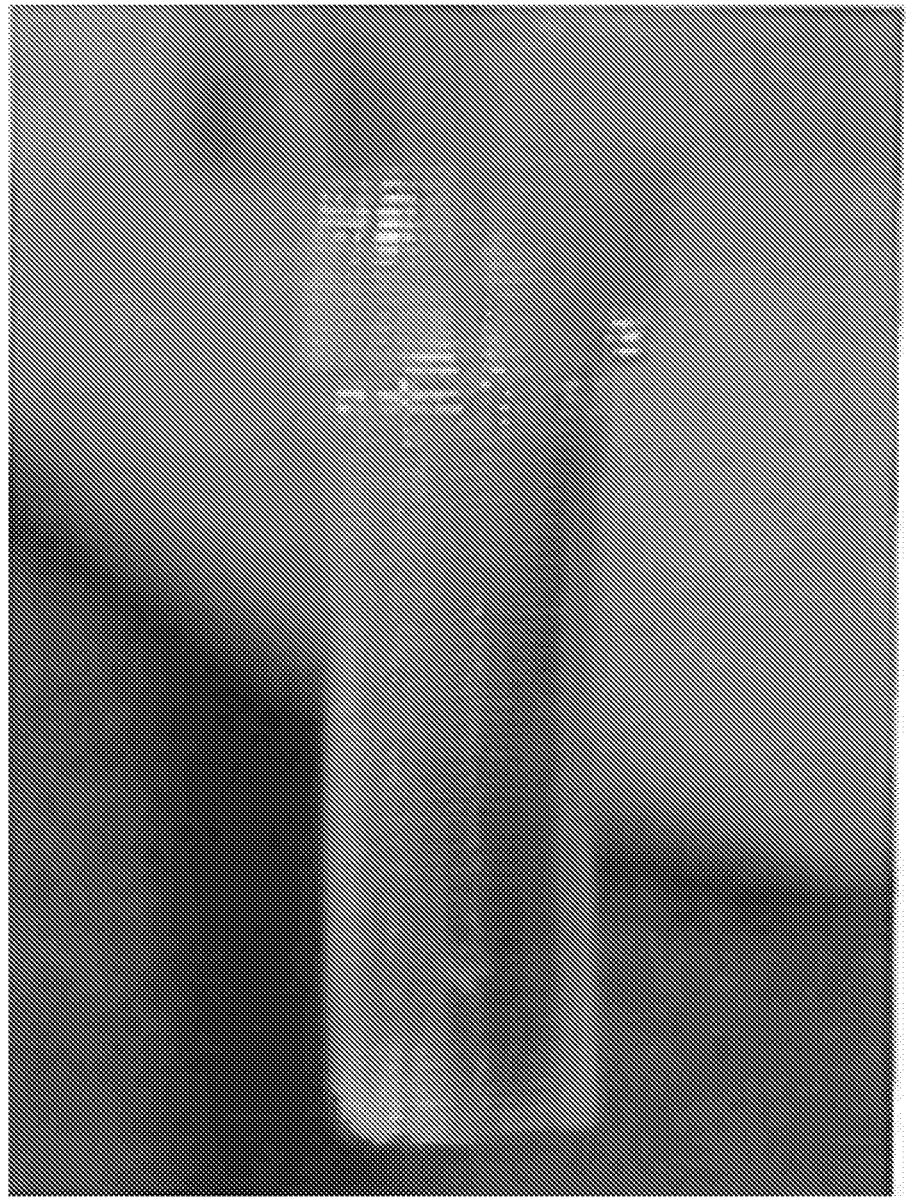
FIG. 8 is an example according to various embodiments illustrating a photograph of a side view of the prosthesis showing a shaft bending issue that occurred in earlier iterations of the prosthetic piece, this highlights one of the major issues when it comes print accuracy.
Figure 9:
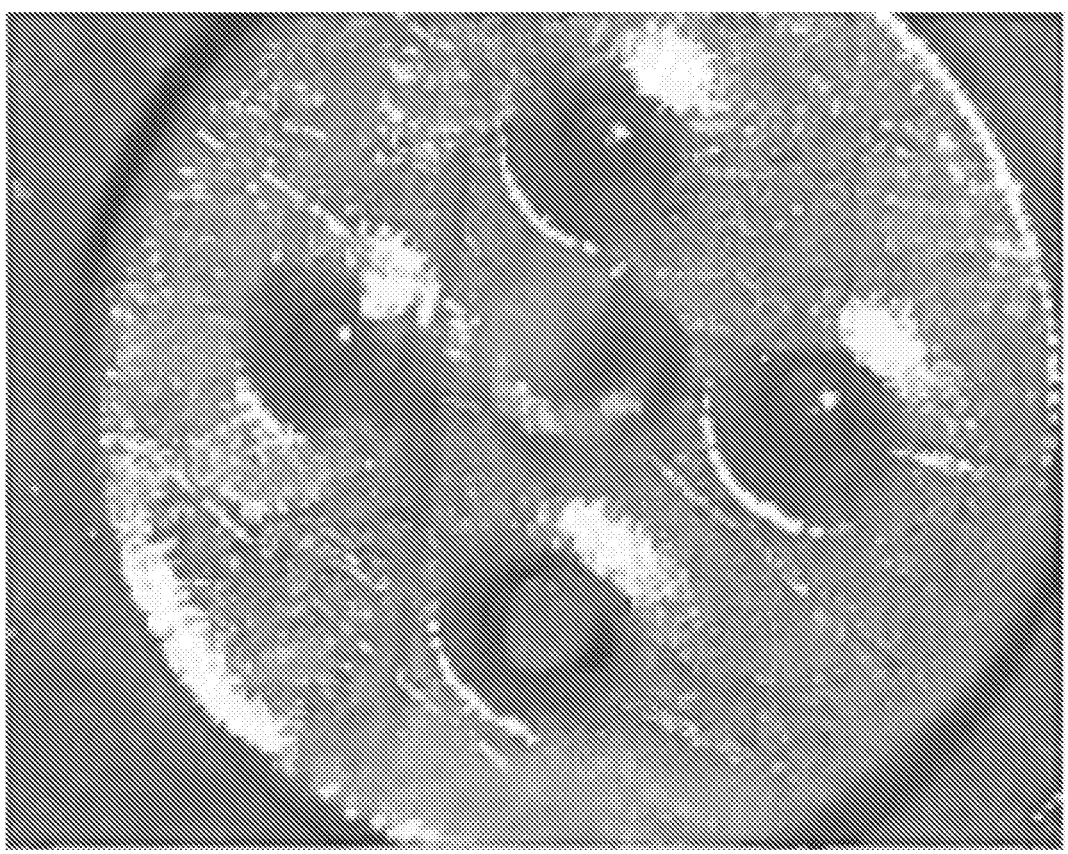
FIG. 9 is an example according to various embodiments illustrating a photograph of a bottom view of the prosthesis showing incomplete or obscured holes in the base after an exposure of greater than 8 seconds.
Figure 10:
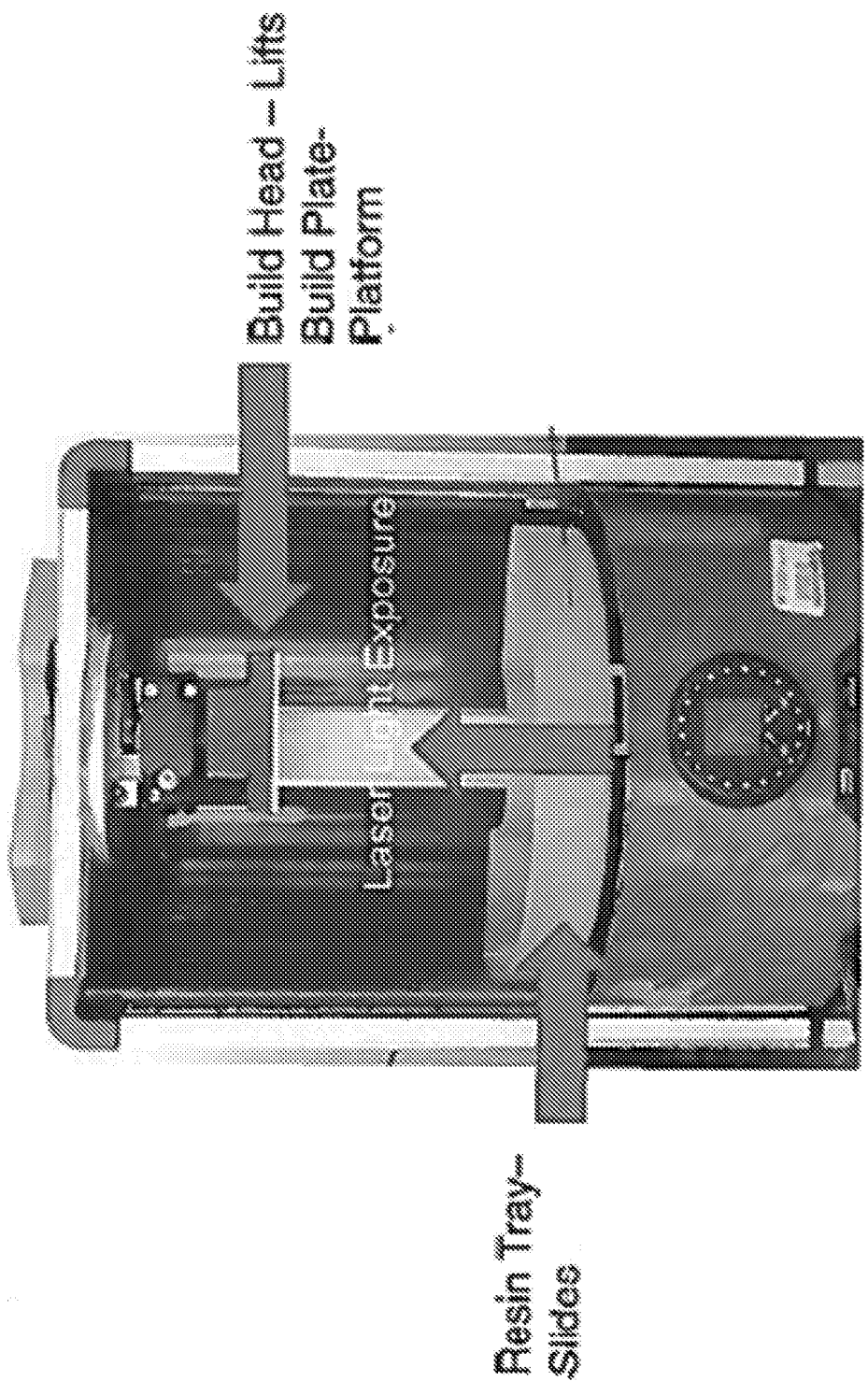
FIG. 10 is an example according to various embodiments illustrating a commercial apparatus, Ember SLA 3D printer, signifying the specific location of the build head, resin tray, and light exposure source.

Some printing defects occurred and are illustrated in FIGS. 8-10. FIG. 7 is an example according to various embodiments illustrating a photograph of a side view of the prosthesis showing a layer shift in the first several layers. High shear force may cause the first few layers to slide due to improper adhesion to the build plate or a loose build head. Such high shear forces may lead to clumping, overlapping, and/or unnecessary curing. The proceeding layers may build upon such defects, which can then lead to deformities in shape, bending of the prosthesis, and/or formation of a wavy layer. Such defects can be problematic, because of the precision required to produce a successful stapes prosthesis. Various embodiments may correct for such defects by adjusting the build head of the 3D printer. For example, the build head may be leveled and tightened, scratches on the build head may be reduced or eliminated to avoid negative effects on adhesion. A coating or scratch free removal may be implemented to reduce friction on the build head and may include such materials as a PTFE polymer spray coating. Various embodiments may reduce and standardize the exposure time and wait time for the first and burn layers respectively from 1-16 s, and 0.01 to 0.05 seconds for wait times. While each individual SLA printer will require some adjustment, there are generic starting points for the exposure times of the layers. Various embodiments reduce the slide velocity parameters, which could otherwise cause newly cured layers to slip before proper adhesion to build head, and cause shear force printing errors.

FIG. 8 is an example according to various embodiments illustrating a photograph of a side view of the prosthesis showing a shaft bending issue that occurred in earlier iterations of the prosthetic piece, this highlights one of the major issues when it comes print accuracy. Without wishing to be bound by theory, the bending due to liquid shear forces. Lateral shift in the layers on one side of the shaft due to shear force may be caused by a sliding motion of the tray in the 3D printer. Various embodiments may avoid this defect by varying the sliding speed, modifying the viscosity of the resin used, and by implementing a pausing time before the sliding motion. Viscosities of the resin are formulation specific and range from about 5-1000 cps depending on the resin manufacturer. Shearing forces may be adding excess force on the prints, leading to parts separating from the head, or experiencing bending forces producing print errors. Various embodiments may also modify the solidification time through exposure and wait time and the build head level as well as the resin viscosity and the tray sliding velocity for the forward and reverse directions. The exposure times in the first and burn layers may be modified, according to various embodiments, to match model layers to maintain consistency in each layer for post print testing.

FIG. 9 is an example according to various embodiments illustrating a photograph of a bottom view of the prosthesis showing incomplete or obscured holes in the base after an exposure of greater than 8 seconds. Hole closure may possible be brought on by resin accumulation where the holes are formed. A defect was caused, as shown in FIG. 8, from resin curing in the empty space of the holes during the formation of the proceeding layers, possibly due to surface tension. Indications of incomplete holes include, but are not necessarily limited to: sloping hole closure, concavity in hole closure, and partial hole formation. To correct for and/or to avoid such defects, various embodiments, reduce the exposure time. For example, by providing a minimal variation of crosslinking between 4 and 16 second prints and/or by reducing the exposure time for the first and burn in layer only. Other embodiments increase the wait time between curing of each layer.

Without wishing to be bound by theory, in most cases shearing forces appeared to be the root cause of the above-mentioned defects. Shear forces may be generated through the sliding of the resin tray during printing. These parameters can be controlled through the settings. As the tray slides from right to left, fluid pushes against the build head and the attached part. Small parts that hang from the build head are vulnerable to shearing forces causing deformation in the part.

FIG. 10 is an example according to various embodiments illustrating a commercial apparatus, Ember SLA 3D printer, signifying the specific location of the build head, resin tray, and light exposure source. This device is an AUTODESK Ember printer, which is no longer commercially sold, but which in general has all the embodiments of any commercial SLA printer. The post UV treatment can be conducted in a variety of ways not limited to; a UV crosslinking device, a UV Light box, A UV cabinet.

FIGS. 14, 15A, 15B, and 16 show the natural stapes prosthesis created and printed using the parameters optimized in the first prosthetic version. More specifically, FIG. 11 is an example according to various embodiments of a Zeiss microscope imaged sample after 8 seconds of exposure time along with a scale bar. FIG. 12A is an example according to various embodiments of a Zeiss microscope imaged sample after 8 seconds of exposure time. FIG. 12B is an example according to various embodiments of the same image in FIG. 11 but flipped to the opposite side along with scale bar. As shown in FIG. 12B dimensionality was maintained on all stapes prostheses printed. Print defects were related to print parameters that may be adjusted. This example, therefore, provides a proof of concept that SLA printing may be adequate for stapes prosthesis printing. Similar material and mechanical considerations are expected upon varying the specific structure printed from the structure of FIG. 2 toward a more customized prosthesis as shown in FIG. 12,13. FIGS. 15A and 15B includes dimensions that are consistent with dimensionality of the CAD design. FIGS. 15B, 16 show defects including on the edge caused by improper removal of the prosthesis from the build head, 16 build head adhesion issues and improper removal. FIG. 13 is an example according to various embodiments of the same image in FIG. 12B, but with certain dimensions annotated to compare for dimensional accuracy.

FIGS. 17A, 17B, and 17C show the natural stapes prosthesis created and printed using the parameters optimized in the first prosthetic version. More specifically, FIG. 14A is an example according to various embodiments of a Zeiss microscope imaged sample after 8 seconds of exposure time along with a scale bar for the bottom of the prosthetic. FIG. 14B is an example according to various embodiments of a Zeiss microscope imaged sample after 8 seconds of exposure time for the top view of the prosthetic with a scale bar. FIG. 14C shows the natural stapes prosthetic created and printed using the optimized parameter in a full view. As shown in FIGS. 14A, 17B, and 17C dimensionality was maintained on all stapes prostheses printed. Print defects were related to print parameters that may be adjusted. This example, therefore, provides a proof of concept that SLA printing may be adequate for stapes prosthesis printing. Similar material and mechanical considerations are expected upon varying the specific structure printed from the structure of FIG. 2 toward a more customized prosthesis as shown in FIGS. 12, and 13.

Various embodiments include reprogramming parameters of the 3D printer to reduce print defects for printing of stapes prostheses. The layer thickness and its effects on printing before and after post-cure processing may be analyzed. Mechanical testing of the stapes parts for impact strength and creep may be conducted. Biocompatible resins may be tested and evaluated in view of the considerations described herein. The suitable biocompatible resins may further be tested for their acoustical properties to ensure proper sound transmission through the printed resins.

What is claimed is:

1. A method for producing a custom-made stapes prosthesis for a patient, the method comprising:
    obtaining a three-dimensional image of a natural stapes bone of the patient; and
    forming a stapes prosthesis that comprises a three-dimensional shape of the natural stapes bone via an additive manufacturing technique based on the three-dimensional image,
    wherein the stapes prosthesis comprises a suitable material that is not osteogenic and is not cytotoxic,
    wherein the stapes prosthesis comprises a plurality of pores having an average size of from about 5 to about 100 micrometers, and
    wherein the stapes prosthesis exhibits a frequency of sound transmission in a range of from about 2 to about 30 kilohertz.

2. The method according to claim 1, wherein the additive manufacturing technique is 3D SLA printing.

3. The method according to claim 1, wherein the suitable material has a density of from about 700 to about 2000 $kg/m^3$.

4. The method according to claim 1, wherein the suitable material has a rigidity modulus of from about 1.75 to about 8.00 GPa.

5. The method according to claim 1, wherein ultrasound waves are able to propagate through the suitable material at a velocity of from about 1,000 m/s to about 2,300 m/s.

6. The method according to claim 1, wherein the suitable material has a Young's modulus of from about $1 \times 10^{10}$ to about $2 \times 10^{10}$ $Nm^{-2}$.

7. The method according to claim 1, wherein the suitable material exhibits a shear modulus that changes from about 3.6 to about 220 kPa when an applied shear stress increases from about 2 to about 140 kPa.

8. The method according to claim 1, wherein the suitable material has a specific mass of from about $1 \times 10^3$ to about $3 \times 10^3$ $kg/m^3$.

9. The method according to claim 1, wherein the suitable material is a polymeric material selected from the group consisting of polyurethane and high-density polyethylene.

* * * * *